United States Patent [19]

Cameron et al.

[11] Patent Number: 4,600,429
[45] Date of Patent: Jul. 15, 1986

[54] GUANIDATED AMINOPHOSPHONIC ACID COMPOUNDS

[75] Inventors: David G. Cameron, Stockholm, Sweden; Harry R. Hudson, London, England; Inger Lagerlund, Bromma, Sweden; Max Pianka, Wembley Park, England; Anita Stroömberg, Saltsjöbaden, Sweden

[73] Assignee: KenoGard AB, Stockholm, Sweden

[21] Appl. No.: 705,342

[22] PCT Filed: Jun. 15, 1984

[86] PCT No.: PCT/SE84/00224
§ 371 Date: Jan. 18, 1985
§ 102(e) Date: Jan. 18, 1985

[87] PCT Pub. No.: WO85/00038
PCT Pub. Date: Jan. 3, 1985

[30] Foreign Application Priority Data

Jun. 17, 1983 [SE] Sweden .................... 8303499-1

[51] Int. Cl.$^4$ .................... C07F 9/38; C07F 9/40; A01N 31/02
[52] U.S. Cl. .................... 71/86; 260/502.5 R; 260/502.5 E; 514/144; 558/176; 558/87
[58] Field of Search .................... 260/502.5 E, 502.5 R, 260/945, 944; 514/144; 71/86

[56] References Cited

U.S. PATENT DOCUMENTS

| | | | |
|---|---|---|---|
| 2,599,807 | 6/1952 | Bersworth | 260/502.5 E |
| 3,322,863 | 5/1967 | Rabourne et al. | 260/502.5 E |
| 3,470,112 | 9/1969 | Irani et al. | 260/502.5 E |
| 3,769,406 | 10/1973 | Anatol et al. | 260/945 |

FOREIGN PATENT DOCUMENTS

| | | | |
|---|---|---|---|
| 6401 | 10/1968 | France | 260/944 |
| 1230121 | 4/1971 | United Kingdom | 260/502.5 E |

OTHER PUBLICATIONS

Oskes et al, "Chem Abstr.", vol. 78, No. 6 (1977) 30806 V (p. 41, col. 1).

*Primary Examiner*—J. E. Evans
*Attorney, Agent, or Firm*—Fred Philpitt

[57] ABSTRACT

Novel guanidated aminophosphonic acid compounds their use as biocides and their intermediates. The compounds are guanidated N-(aminoalkyl) aminoalkanephosphonic acid derivatives and are characterized in that they comprise both a phosphonic acid type group and at least one guanidino group and also in that they are based on alkylene amines. The compounds have the general formula:

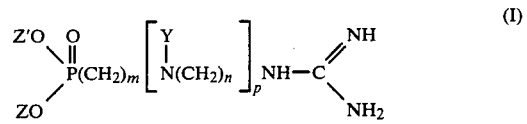

(I)

wherein Z and Z' are hydrogen, a lower alkyl group or an alkali metal, Y is hydrogen or an amidine group, m is 1–3, n is 4–16 and p is 1–3. The compounds can be prepared by reacting a halogenoalkanephosphonic acid compound with an alkylene di- or polyamine followed by guanidation of the so obtained product. The compounds are particularly useful as fungicides and especially as fungicides for industrial purposes.

5 Claims, No Drawings

GUANIDATED AMINOPHOSPHONIC ACID COMPOUNDS

The present invention relates to novel guanidated aminophosphonic acid compounds and to the use of these compounds as biocides. The invention further relates to a process for the preparation of the guanidated aminophosphonic acid compounds and to novel aminophosphonic acid compounds useful as intermediates in this process.

The novel compounds of the invention have the general formula

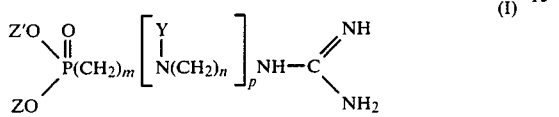 (I)

wherein Z and Z', which may or may not be equal, are hydrogen, a lower alkyl group having 1 to 4 carbon atoms or an alkali metal, Y is hydrogen or an amidine group, m is 1 to 3, n is 4 to 16 and p is 1 to 3. The invention also covers acid addition salts.

The compounds of the above given formula can be classed as guanidated N-(aminoalkyl)aminoalkanephosphonic acid derivatives and in the formula the lower alkyl esters, half esters and also the alkali metal mono- or di- salts are included.

The compounds are characteristic in that they contain both a phosphonic acid type group,

and at least one guanidino group,

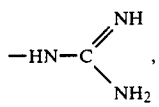

and in that they are based on alkylene amines.

The pure compounds of the free phosphonic acids are fine white crystalline solids, and they are all soluble in water. The solubility in water decreases somewhat with increasing chain lengths. The esters are less soluble in water but soluble in alcohols and other solvents. As a rule the acid addition salts of the guanidated aminophosphonic acid compounds are much more soluble in water than the free acids and also more soluble in alcohols.

Preferred compounds are those containing alkylene groups having from 4 to 14 carbon atoms, and especially from 6 to 14 carbon atoms. Further, compounds of the general formula I given above wherein p equals 1 are preferred, i.e. the compounds based on alkylene diamines. Compounds wherein m is 1 are preferred to those wherein m equals b 2 or 3.

It should be understood that when p is 2 or 3, n does not necessarily have to be the same for the different alkylene groups. These might of course vary as a result of the use of technical amines having varying chain lengths as starting material. It should further be understood that when p is 2 or 3, either one, two or three of the Y-groups may be amidine groups,

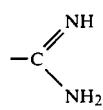

the rest being hydrogen. This depends on the guanidation reagent used in the preparation process and will be described more in detail below. However, compounds wherein all groups Y are hydrogen are preferred.

The invention also relates to a method for the preparation of guanidated N-(aminoalkyl)aminoalkanephosphonic acid derivatives of the above given formula (I), said method comprising reacting a halogenoalkanephosphonic acid compound with an alkylene di- or polyamine and guanidation of the so obtained product.

The first step of the preparation method comprises reacting a halogenoalkanephosphonic acid compound having the formula

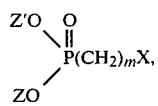

wherein Z and Z', as above, independent of each other are hydrogen, a lower alkyl group having 1 to 4 carbon atoms or an alkali metal, and m is 1 to 3, preferably 1, and wherein X is a halogen, suitably chlorine or bromine and most preferably chlorine, with an alkylene di- or polyamine of the formula.

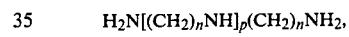

wherein n is 4 to 16 and p is 0, 1 or 2. Diamines of this type are suitably used as starting material.

The reaction between the halogenoalkanephosphonic acid compound and the amine is carried out in aqueous solution and at an elevated temperature. The temperature is suitably within the range of from 50° to 100° C. and preferably from 70° to 100° C. The reaction rate will of course vary with the temperature and also with the starting materials; usually a reaction time of up to about 20 hours will be sufficient. The reaction can be carried out under reflux. After the reaction is completed water and optionally excess of unreacted amine are removed, e.g. by distillation, and the product is isolated.

The aminoalkylaminophosphonic acid derivatives of the general formula

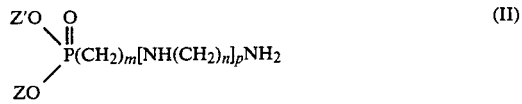 (II)

are then guanidated using conventional guanidation reagents such as cyanamide, O-alkylisoureas, S-alkylisothioureas or salts of these etc. The temperature at the guanidation is not critical but may vary within wide limits, from room temperature up to about 100° C. The guanidation step is carried out under neutral or alkaline conditions and when the reaction is completed the reaction product solution is neutralized. The compounds can then be crystallized for isolation.

The above general preparation method applies to all the compounds. As concerns the acid addition salts these will vary with the guanidation reagent used and so will the number of guanidated amino groups. The acid addition salt will further vary with the neutralizing agents used in the process. In the first reaction step the molar ratio of di- or polyalkylene amine to halogenophosphonic acid compound is suitably within the range of from 2:1 to 8:1 and preferably within the range of from 4:1 to 6:1. In the guanidation step it is usually sufficient to have a ratio of 1:1 between the guanidation reagent and the amino groups to be guanidated, although an excess of the guanidation reagent may be used.

As shown in the general formula I the novel compounds of the present invention may contain both guanidated primary and secondary amino groups. Compounds containing one or several guanidated secondary amino groups, i.e. those in which Y is an amidine group, may be prepared using cyanamide as guanidation reagent. In contrast to the urea derivatives cyanamide is an unspecific guanidation reagent and will randomly guanidate both primary and secondary amino groups, while the ureas will predominantly guanidate the primary amino groups.

The aminoalkylaminophosphonic acid compounds of the general formula (II)

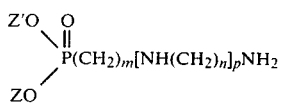

wherein Z and Z', which may or may not be equal, are hydrogen, a lower alkyl group having 1 to 4 carbon atoms or an alkali metal, m is 1 to 3, n is 4 to 16 and p is 1 to 3, which are intermediates in the preparation of the guanidated aminophosphonic acid compounds, are novel and claimed per se. n is suitably 6 to 14.

The novel guanidated compounds of the present invention can be in the form of the free phosphonic acids or phosphonates or in the form of acid addition salts. Both salts of mineral acids and organic acids can be prepared. When cyanamide is used as the guanidation reagent the acid addition salt is suitably prepared by adding the desired acid in or after the guanidation step and when ureas are used as guanidation reagents an isouronium compound or isothiouronium compound is selected for the preparation of acid addition salts. As examples of salts of organic acids can be mentioned those of lower organic acids such as formates and acetates, those of higher organic acids such as oleates and stearates. Benzoates may also be used. The type of acid salt will of course also have to be selected with respect to the intended use of the compound in order not to have any negative effects in this use.

Particularly claimed compounds according to the invention are the novel compounds of formula I wherein Z and Z' both are hydrogen, m is 1 or 2, n is 6 to 14 and p is 1 and the corresponding intermediates of formula II wherein Z and Z' both are hydrogen, m is 1 or 2, n is 6 to 14 and p is 1.

The invention also covers the use of the guanidated aminophosphonic acid compounds as biocides, and particularly as plant protecting agents, antimicrobial agents and insecticides. For this purpose it is in most cases sufficient to use the crude reaction product resulting from the reaction between the halogenoalkanephosphonic acid or phosphonate and the amine in the guanidation step without an intermediate recrystallisation.

The guanidated product will then contain the novel compounds of the invention as the main component and the rest will consist of guanidated di- or higher alkyleneamines and of intermediate unguanidated aminoalkylaminophosphonic acid compounds. Guanidated di- or higher alkyleneamines are previously known to have biocidal effect and it has been found that the intermediate aminophosphonic acid compounds of the present invention in some cases possess biocidal effect and this makes it possible to utilize a crude reaction product. The products, or compounds, can be formulated in conventional manner and used with inert carriers or diluents. They may be useful in several areas; for example as bactericides, fungicides, insecticides, herbicides etc. The compounds are particularly useful as fungicides both for industrial purposes, in wood treatment and especially as fungicides for agricultural and horticultural purposes. The use of the compounds as fungicides in agriculture and horticulture, and especially as foliar fungicides is a preferred embodiment of the invention. It should also be mentioned that the compounds have other utilities; they might for example be used as chelating agents.

The invention is further illustrated in the following examples which, however, are not intended to limit the same.

EXAMPLE 1

A. Preparation of
N-(12-aminododecyl)-aminomethanephosphonic monohydrate. Compound 1 A.

Chloromethanephosphonic acid (15.1 g, 115.7 mmoles) and 1,12-diaminododecane (100 g, 0.5 moles) were heated under reflux in water (160 cm$^3$) for 20 hours. The water was then distilled off and ethanol (250 cm$^3$) was added. The phosphonic acid was filtered off and dried. The crude yield was 30.7 g (85%). A sample was purified by recrystallization from water/ethanol to give N-(12-aminododecyl)-aminomethanephosphonic acid monohydrate as a fine white crystalline solid having a melting point of 234° C.

B. Preparation of
N-(12-guanidinododecyl)-aminomethanephosphonic acid monohydrate. Compound 1 B.

N-(12-aminododecyl)-aminomethanephosphonic acid monohydrate (2.5 g, 8 mmoles), sodium hydroxide (1.3 g, 38 mmoles) and S-methylisothiouronium chloride (2.0 g, 16.4 mmoles were dissolved in water (120 cm$^3$) and heated at 90° C. for 4 hours. The solution was acidified to pH 1 with hydrochloric acid and evaporated. Methanol (100 cm$^3$) was added and sodium chloride was filtered off. The filtrate was neutralized to pH 6 with propylene oxide. The solid so formed was filtered off and washed with methanol (50 cm$^3$).

The crude yield after drying of guanidinophosphonic acid was 2.6 g (91%). A sample was recrystallized from hot water to give N-(12-guanidinododecyl)-aminomethanephosphonic acid monohydrate as a fine white crystalline solid having a melting point of 129°–130° C.

EXAMPLE 2

A. Preparation of
N-(6-aminohexyl)-aminomethanephosphonic acid monohydrate. Compound 2 A.

Chloromethanephosphonic acid (6.5 g, 49.8 mmoles) and 1.6-diaminohexane (34.8 g, 300 mmoles) were dissolved in water (130 cm³) and heated under reflux for 20 hours. The water was removed and ethanol (250 cm³) was added to the solid residue. The phosphonic acid was filtered off and dried. The crude yield was 10.4 g (92%). A sample was purified by recrystallization from water/ethanol to give N-(6-aminohexyl)-aminomethanephosphonic acid monohydrate as a fine white crystalline solid having a melting point of 235° C.

B. Preparation of
N-(6-guanidinohexyl)-aminomethanephosphonic acid monohydrate. Compound 2 B.

N-(6-aminohexyl)-aminomethanephosphonic acid monohydrate (6.1 g, 26.7 mmol), sodium hydroxide (4.15 g, 104 mmoles) and S-methylisothiouronium chloride (6.3 g, 49.8 mmoles) were dissolved in water (50 cm³) and heated at 60° C. for 4 hours. The solution was acidified to pH 1 with hydrochloric acid and evaporated. Methanol (50 cm³) was added and sodium chloride was filtered off. The filtrate was neutralized to pH 6 with propylene oxide.

The sticky precipitate was dissolved in cold water (50 cm³) and acetone added dropwise until the solution just became opaque. A few drops of water were added to clear the solution which was then stored in a fridge for several days. The crystals formed were filtered off, washed with acetone and dried in a vacuum oven at 60° C. to yield N-(6-guanidinohexyl)-aminomethanephosphonic acid monohydrate (4.3 g, 60%) as a fine white crystalline solid having a melting point of 182° C.

EXAMPLE 3

A. Preparation of
N-(10-aminodecyl)-aminomethanephosphonic acid monohydrate. Compound 3 A.

Chloromethanephosphonic acid (5.5 g, 42 mmoles) and 1.10-diaminodecane (44 g, 255 mmoles) were heated under reflux in water (200 cm³) for 20 hours. The water was removed and ethanol (400 cm³) added to the solid residue. The phosphonic acid was filtered off and dried. The crude yield was 11.4 g (87%). A sample was purified by recrystallization from water/ethanol to give N-(10-aminodecyl)-aminomethanephosphonic acid monohydrate as a fine white crystalline solid having a melting point of 238° C.

B. Preparation of
N-(10-guanidinodecyl)-aminomethanephosphonic acid monohydrate. Compound 3 B.

N-(10-aminodecyl)-aminomethanephosphonic acid monohydrate (4.1 g, 14.4 mmoles), S-methylisothiouronium chloride (3.65 g, 28.9 mmoles) and sodium hydroxide (2.8 g, 70 mmoles) were dissolved in water (100 cm³) and heated in an oil bath at 70° C. for 4 hours. The clear solution was then acidified to pH 1 with concentrated hydrochlorid acid and the volatile components were removed on a rotary evaporator. The oily residue was dissolved in methanol (100 cm³) and sodium chloride filtered off (3.4 g, 83%). Propylene oxide was then added to the filtrate until pH 6.

The crude guanidinophosphonic acid was washed with methanol (50 cm³) and dried. The yield was 4.2 g (89%). Recrystallization from water/acetone and drying at 60° C. gave N-(10-guanidinodecyl)-aminomethanephosphonic acid monohydrate (3.8 g, 81%) as a fine white crystalline solid having a melting point of 133°–134° C.

EXAMPLE 4

A. Preparation of
N-(8-aminooctyl)-2-aminoethanephosphonic acid monohydrate. Compound 4 A.

Diethylbromoethanephosphonate (15.3 g, 0.062 moles) and 1.8-diaminooctane (54.0 g, 0.375 moles) were heated under reflux in water (250 cm³) for 5 hours. The water and excess diamine were then distilled off. Concentrated hydrochloric acid (280 cm³) was added and the solution heated under reflux for 8 hours. The solution was then evaporated to dryness on a rotary evaporator and the residue was dissolved in methanol (75 cm³) and propylene oxide wad added to pH 6. The phosphonic acid was filtered off and dried. The crude yield was 10.2 g (60.5%). A sample was purified by recrystallization from water/ethanol to give N-(8-aminooctyl)-2-aminoethanephosphonic acid monohydrate as a fine white crystalline solid having a melting point of 210° C.

B. Preparation of
N-(8-guanidinooctyl)-2-aminoethanephosphonic acid monohydrate. Compound 4 B.

N-(8-aminooctyl)-2-aminoethanephosphonic acid monohydrate (4.0 g, 0.0148 moles), S-methylisothiouronium chloride (3.75 g, 0.0296 moles) and potassium hydroxide (3.32 g, 0.0592 moles) were dissolved in water (60 cm³) and heated in an oil bath at 80° C. for 4.5 hours. The clear solution was then acidified to pH 2 with concentrated hydrochloric acid and the volatile components were removed on a rotary evaporator. The oily residue was dissolved in methanol (75 cm³) and potassium chloride filtered off (3.5 g, 79.3%). Propylene oxide was then added to the filtrate until pH 6. The sticky precipitate was dissolved in cold water (50 cm³) and acetone added dropwise until the solution just became opaque. A few drops of water were added to clear the solution which was then stored in a fridge for several days. The crystals formed were filtered off, washed with acetone and dried in a vacuum oven at 60° C. to yield N-(8-guanidinooctyl)-2-aminoethanephosphonic acid monohydrate (2.7 g, 58.4%) as a fine white crystalline solid having a melting point of 108° C.

EXAMPLE 5

A. Preparation of
N-(8-aminooctyl)-aminomethanephosphonic acid monohydrate. Compound 5 A.

Chloromethanephosphonic acid (7.5 g, 58 mmoles) and 1.8-diaminooctane (50.0 g, 347 mmoles) were dissolved in water (130 cm³) and heated under reflux for 20 hours. The water was then removed and ethanol (250 cm³) added to the solid residue. The phosphonic acid was filtered off and dried. The crude yield was 13.3 g (90%). A sample was purified by recrystallization from water/ethanol to give N-(8-aminooctyl)-aminomethanephosphonic acid monohydrate as fine white solid having a melting point of 242° C.

B. Preparation of
N-(8-guanidinooctyl)-aminomethanephosphonic acid monohydrate. Compound 5 B.

N-(8-aminooctyl)-aminomethanephosphonic acid monohydrate (5.6 g, 21.9 mmoles), S-methylisothiouronium chloride (5.53 g, 43.7 mmoles) and potassium hydroxide (4.9 g, 87.3 mmoles) were dissolved in water (50 cm³) and heated in an oil bath at 60° C. for 4 hours. The solution was cooled and acidified to pH 1 with concentrated hydrochloric acid. The volatile components were removed on a rotary evaporator and methanol (50 cm³) added to the residue. Potassium chloride (5.9 g, 80% after drying) was filtered off and propylene oxide added to the filtrate until pH 6.

The supernatant liquors were decanted off from the oil formed on addition of the propylene oxide and the oil washed with methanol (50 cm³). Acetone (75 cm³) was added and the solvents removed on a rotary evaporator. The solid so formed was dried in a vacuum oven at 60° C. (5 hours), to give crude guanidinophosphonic acid (5.8 g, 89%). Recrystallization from water/acetone gave N-(8-guanidinooctyl)-aminomethanephosphonic acid monohydrate (3.9 g, 60%) as a fine white crystalline solid having a melting point of 170° C.

EXAMPLE 6

A. Preparation of N-(4-aminobutyl)-aminomethanephosphonic acid monohydrate. Compound 6 A.

Chloromethanephosphonic acid (7.0 g, 53.6 mmoles) and 1,4-diaminobutane (30.0 g, 340 mmoles) were heated under reflux in water (200 cm³) for 20 hours. The water was then distilled off and acetone (110 cm³) was added. The phosphonic acid was filtered off and dried. The crude yield was 9.8 g (91%). A sample was purified by recrystallization from water/ethanol to give N-(4-aminobutyl)-aminomethanephosphonic acid monohydrate as a fine white crystalline solid having a melting point of 258° C.

B. Preparation of N-(4-guanidinobutyl)-aminomethanephosphonic acid monohydrate. Compound 6 B.

N-(4-aminobutyl)-aminomethanephosphonic acid monohydrate (3.8 g, 19 mmoles), sodium hydroxide (3.0 g, 76 mmoles) and S-methylisothiouronium chloride (4.8 g, 38 mmoles) were dissolved in water (50 cm³) and heated at 70° C. for 4 hours. The solution was acidified to pH 1 with hydrochloric acid and evaporated. Methanol (100 cm³) was added and sodium chloride was filtered off. The filtrate was neutralized to pH 6 with propylene oxide. The sticky precipitate was dissolved in a minimum of cold water and acetone added dropwise until the solution just became opaque. A few drops of water were added to clear the solution which was then stored in a fridge for several days. The crystals formed were filtered off, washed with acetone and dried in a vacuum oven at 60° C. to yield N-(4-guanidinobutyl)-aminomethanephosphonic acid monohydrate (2.9 g, 63%) as a fine white crystalline solid having a melting point of 160°-161° C.

EXAMPLE 7

Preparation of N-(9-aminononyl)aminomethanephosphonic acid monohydrate. Compound 7A.

Chloromethanephosphonic acid (4.0 g, 30.6 mmoles) and 1.9-diaminononane (20.1 g, 127.2 mmoles) were dissolved in water (100 cm³) and the resultant solution heated under reflux for 20 hours. The water was then distilled off and methanol (80 cm³) added to the residue. The solid was filtered off, washed with methanol (2×50 cm³) and dried in a vacuum oven at 60° C. for three hours to yield the crude N-(9-aminononyl)aminomethanephosphonic acid monohydrate (6.5 g, 78.5%), having a melting point of 240°-241° C.

EXAMPLE 8

Preparation of the di-potassium salt of N-(8-guanidino-octyl)aminomethanephosphonic acid. Compound 8.

N-(8-guanidino-octyl)aminomethanephosphonic acid monohydrate (3.0 g, 10.07 mmoles) and potassium hydroxide (1.13 g, 20.14 mmoles) were dissolved in water (100 cm³). The water was then distilled off and methanol (80 cm³) added to the residue. Filtration and then evaporation of the methanol, followed by drying in a vacuum oven at 60° C. for three hours gave the crude di-potassium salt as a white solid (2.7 g, 71.7%).

Identification of compounds

The structures of the compounds were ascertained by nuclear magnetic resonance ($^1$H-, $^{13}$C-, $^{15}$N- and $^{31}$P-) spectra and mass spectra. All compounds give very strong $(M+1)^+$-peaks (in most cases the base peak) using FAB-(Fast Atom Bombardment) mass spectrometry, see below

| Compound | Molecular weight | $(M + 1)^+$ |
| --- | --- | --- |
| 1A | 294 | 295 |
| 2A | 210 | 211 |
| 3A | 266 | 267 |
| 4A | 252 | 253 |
| 5A | 238 | 239 |
| 6A | 182 | 183 |
| 1B | 336 | 337 |
| 2B | 252 | 253 |
| 3B | 308 | 309 |
| 4B | 294 | 295 |
| 5B | 280 | 281 |

EXAMPLE 7

Fungicidal activity test

Compounds prepared as above were screened for their fungicidal activity.

The fungicidal activity of the substances was examined using a mycelial growth inhibition test on agar according to the following method.

The substances were dissolved in sterilized potatoe dextrose agar (PDA) to give concentrations of 500 and 1000 ppm respectively. The mixtures were then poured onto standard petri dishes with 9 cm diameter. A 5 mm diameter agar plug with lively growing mycelia (cultivated on PDA) was placed in the center of each petri dish. After incubation at +28° C. for 7 to 21 days (depending on the growth rate of the respective fungus) the growth diameter was measured and compared with that of untreated dishes.

Several plant pathogenic fungi belonging to different subdivisions and representative of important crop diseases were used in the tests.

In the tables below the results are shown by classifying the compounds according to the following scale: 0=0–25% inhibition of growth, 1=26–50% inhibition of growth, 2=51–75% inhibition of growth, 3=76–99% inhibition of growth, 4=100% inhibition of growth.

TABLE 1

| Fungus | Dosage (ppm) | Efficacy of Compound | | |
|---|---|---|---|---|
| | | 1 B | 3 B | 5 B |
| Pyricularia oryzae | 500 | 1 | 4 | 2 |
| Botrytis cinerea | 500 | 3 | 4 | 0 |
| Rhizoctonia solani | 500 | 1 | 1 | 0 |
| Rhizoctonia solani | 1000 | 4 | 2 | n.t. |
| Septoria nodorum | 500 | 1 | 4 | 1 |
| Septoria nodorum | 1000 | 2 | 4 | 2 |
| Drechslera sativa | 500 | 3 | 4 | n.t. |
| Drechslera sativa | 1000 | 3 | 4 | 3 |
| Fusarium avenaceum | 1000 | 2 | 2 | n.t. |

Note: n.t. = not tested

TABLE 2

| Fungus | Dosage (ppm) | Efficacy of Compound | | | | | | | |
|---|---|---|---|---|---|---|---|---|---|
| | | 1A | 2A | 3A | 4A | 5A | 6A | 2B | 4B |
| Drechslera sativa | 500 | n.t. | n.t. | 3 | 3 | n.t. | n.t. | n.t. | 2 |
| " | 1000 | 4 | 2 | 3 | 3 | 2 | 2 | 2 | n.t. |
| Septoria nodorum | 500 | 0 | 3 | 1 | 0 | 0 | 2 | n.t. | 0 |

Note: n.t. = not tested

We claim:

1. Guanidated N-(aminoalkyl)aminoalkanephosphonic acid derivatives having the general formula

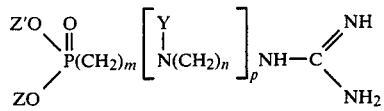

wherein Z and Z', which may or may not be equal, are hydrogen, a lower alkyl group having 1 to 4 carbon atoms or an alkali metal, Y is hydrogen or an amidine group, m is 1 to 3, n is 4 to 16 and p is 1 to 3, or their acid addition salts.

2. Compounds according to claim 1, wherein p is 1.

3. Compounds according to claim 1, wherein m is 1.

4. Compounds according to claim 1, wherein Z and Z' are hydrogen.

5. Use of guanidated N-(aminoalkyl)aminoalkanephosphonic acid derivatives having the general formula $$\begin{array}{c} Z'O \\ \diagdown \\ \phantom{Z}\phantom{O}P(CH_2)_m \\ \diagup \\ ZO \end{array} \left[ \begin{array}{c} Y \\ | \\ N(CH_2)_n \end{array} \right]_p NH-C \begin{array}{c} \diagup NH \\ \diagdown NH_2 \end{array}$$

wherein Z and Z', which may or may not be equal, are hydrogen, a lower alkyl group having 1 to 4 carbon atoms or an alkali metal, Y is hydrogen or an amidine group, m is 1 to 3, n is 4 to 16 and p is 1 to 3, or their acid addition salts, as biocides.

* * * * *